United States Patent
Kumaraswamy et al.

(10) Patent No.: US 11,925,730 B2
(45) Date of Patent: Mar. 12, 2024

(54) METHOD FOR PREVENTING RECTRACTION OF AQUEOUS DROPS AND A MEDICAL DEVICE COATED WITH HYDROPHILIC COATING

(71) Applicant: COUNCIL OF SCIENTIFIC & INDUSTRIAL RESEARCH, New Delhi (IN)

(72) Inventors: Guruswamy Kumaraswamy, Pune (IN); Manoj Kumar, Pune (IN); Mayuresh Arvind Kulkarni, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 356 days.

(21) Appl. No.: 16/316,844

(22) PCT Filed: Jul. 11, 2017

(86) PCT No.: PCT/IN2017/050288
§ 371 (c)(1),
(2) Date: Jan. 10, 2019

(87) PCT Pub. No.: WO2018/011824
PCT Pub. Date: Jan. 18, 2018

(65) Prior Publication Data
US 2019/0290805 A1 Sep. 26, 2019

(30) Foreign Application Priority Data
Jul. 13, 2016 (IN) .............................. 201611023934

(51) Int. Cl.
| | | |
|---|---|---|
| A61L 29/08 | (2006.01) |
| A61L 29/14 | (2006.01) |
| A61L 29/16 | (2006.01) |
| A61L 31/10 | (2006.01) |
| A61L 31/14 | (2006.01) |
| A61L 31/16 | (2006.01) |
| C09D 5/00 | (2006.01) |

(52) U.S. Cl.
CPC ............. *A61L 29/085* (2013.01); *A61L 29/14* (2013.01); *A61L 29/16* (2013.01); *A61L 31/10* (2013.01); *A61L 31/14* (2013.01); *A61L 31/16* (2013.01); *C09D 5/00* (2013.01); *A61L 2300/406* (2013.01); *A61L 2400/10* (2013.01); *A61L 2420/02* (2013.01); *A61L 2420/06* (2013.01)

(58) Field of Classification Search
CPC .............. A61K 49/006; A61K 49/0021; A61K 49/003; A61B 5/0036; A61B 5/0071; A61B 5/0075
See application file for complete search history.

(56) References Cited

U.S. PATENT DOCUMENTS

| | | | |
|---|---|---|---|
| 5,025,004 A * | 6/1991 | Wu ........................ | A61K 8/06 106/170.12 |
| 5,945,409 A * | 8/1999 | Crandall .................. | A61K 8/90 514/159 |
| 6,610,035 B2 | 8/2003 | Yang et al. | |
| 7,015,262 B2 | 3/2006 | Leong | |
| 2003/0207987 A1 | 11/2003 | Leong | |
| 2011/0144578 A1* | 6/2011 | Pacetti .................. | A61L 29/085 604/96.01 |
| 2013/0197435 A1 | 8/2013 | Wang | |
| 2015/0164117 A1* | 6/2015 | Kaplan ................ | A61K 8/0208 424/490 |
| 2015/0359945 A1* | 12/2015 | Rosenblatt ............ | A61L 31/145 424/404 |

FOREIGN PATENT DOCUMENTS

| | | | | |
|---|---|---|---|---|
| EP | 2 241 341 A2 | 10/2010 | | |
| WO | WO-9828390 A1 * | 7/1998 | ............. | C11D 1/825 |
| WO | 2000/067816 A1 | 11/2000 | | |
| WO | 2005/039770 A | 5/2005 | | |
| WO | 2011/071629 A1 | 6/2011 | | |
| WO | 2014/066085 A1 | 5/2014 | | |

OTHER PUBLICATIONS

Hollies, N. R. S., et al. "Improved Comfort Polyester: Part IV: Analysis of the Four Wearer Trials." Textile Research Journal 54.8 (1984): 544-548 (Year: 1984).*
Vance Bergeron, et al.; Controlling droplet deposition with polymer additives; published in Nature; vol. 405; Jun. 15, 2000; pp. 772-775.
Mounir Aytouna, et al; Impact dynamics of surfactant laden drops: dynamic surface tension effects; published in Experiments in Fluids; 2010; 48 (1); pp. 49-57.
N. Mourougou-Candoni, et al.; Retraction phenomena of surfactant solution drops upon impact on a solid substrate of low surface energy, published in Langmuir; 1999; 15 (19); pp. 6563-6574.
Katarzyna Szymczyk, et al.; Wettability of a Glass Surface in the Presence of Two Nonionic Surfactant Mixtures, published in Langmuir; 2008; 24(15); pp. 7755-7760.

(Continued)

*Primary Examiner* — James W Rogers
(74) *Attorney, Agent, or Firm* — LADAS & PARRY LLP

(57) ABSTRACT

The present invention discloses a method for preventing retraction of aqueous drops on a hydrophobic surface. The present invention also discloses a medical device coated with a hydrophilic coating comprising a substrate and a coating composition.

4 Claims, 5 Drawing Sheets

(56) References Cited

OTHER PUBLICATIONS

Figure 1D:
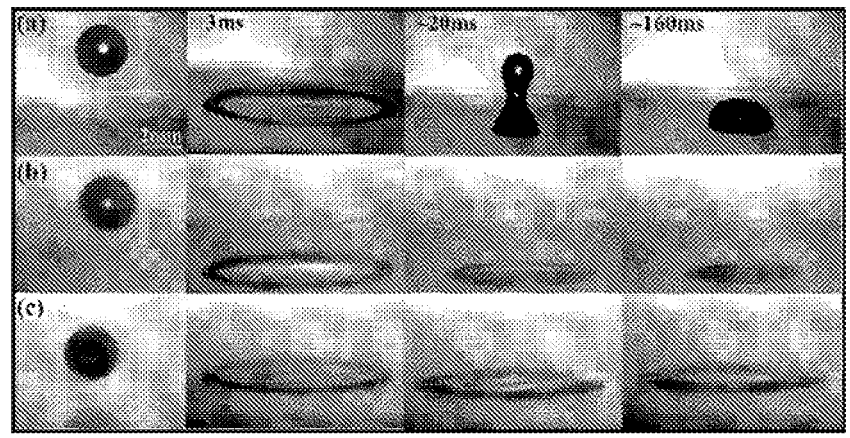

Meirong Song, et al.; Controlling liquid splash on superhydrophobic surfaces by a vesicle surfactant; published in Science Advances; 2017; 3 e1602188; Mar. 1, 2017.

Maher Damak, et al.; Enhancing droplet deposition through in-situ precipitation; published in Nature Communications; 2016; 7:12560; DOI: 10.1038/ncomms12560; www.nature.com/naturecommunications.

International Search Report (ISR) for International Application No. PCT/IN2017/050288.

Written Opinion (WO) for International Application No. PCT/IN2017/050288 dated Dec. 1, 2017.

\* cited by examiner

Fig: 1(a), (b), (c)

METHOD FOR PREVENTING RECTRACTION OF AQUEOUS DROPS AND A MEDICAL DEVICE COATED WITH HYDROPHILIC COATING

RELATED APPLICATION

This application is a national phase entry under 35 USC 371 of International Patent Application No.: PCT/IN2017/050288 filed on 11 Jul. 2017, which claims priority from Indian Application No. 201611023934 filed on 13 Jul. 2016, the disclosures of which are incorporated in their entirety by reference herein.

FIELD OF THE INVENTION

The present invention relates to a method for preventing retraction of aqueous drops and application thereof. More particularly, the present invention relates to a method for preventing retraction of aqueous drops on a hydrophobic surface and a medical device coated with hydrophilic coating comprising a substrate and a coating composition.

BACKGROUND OF THE INVENTION

Drops impacting onto solid surfaces are important for a large number of applications: for instance, almost all spray coating and deposition processes rely ultimately on the interaction of a droplet with a surface. In a wide variety of applications, hydrophobic surfaces need to be stained using an aqueous dispersion. The efficacy of spreading of aqueous dispersions on hydrophobic substrates is low due to the water drops bouncing off or splashing. A large variety of phenomena can be present during drop impacts, from splashing to spreading, and from large wave surface deformation to rebound. Efficient delivery of aqueous sprays to hydrophobic surfaces is the key technological challenge in a wide variety of applications, including pesticide delivery to plants. To account for losses due to bouncing of pesticide sprays off hydrophobic leaf surfaces, large excess of pesticide is typically employed, resulting in environmentally hazardous run-offs that contaminate soil and ground water.

Synergystic interactions between surfactants occur when two surfactants used in concert provide unexpected surface characteristics beyond those which would be predicted based on the sum of the surface properties of the individual components. Synergystic surfactant mixtures not only have the areas of utility in detergents, emulsifiers, foamers, wetting agents, dispersants, flocculants and penetrants, but also have the added advantage of being able to affect these utilities at lower concentrations. This advantage may be exploited in a variety of ways such as the improved economics of using less material to achieve the same performance, or by extending the effective lifetime of a surfactant solution at a given concentration.

Article titled "Controlling droplet deposition with polymer additives" by V Bergeron et al. published in *Nature,* 2000, 405, pp 772-775 reports by adding very small amounts of a flexible polymer to the aqueous phase, which will inhibit droplet rebound on a hydrophobic surface and markedly improve deposition without significantly altering the shear viscosity of the solutions.

Article titled "Impact dynamics of surfactant laden drops: dynamic surface tension effects" by M Aytouna published in *Experiments in Fluids,* 2010, 48 (1), pp 49-57 reports the impact and subsequent retraction of aqueous surfactant-laden drops upon high-speed impact on hydrophobic surfaces. Without surfactants, a rapid expansion of the drop due to the fluid inertia is followed by a rapid retraction, due to the wetting incompatibility. With surfactants, the retraction can be partly inhibited.

Article titled "Retraction phenomena of surfactant solution drops upon impact on a solid substrate of low surface energy" by N Mourougou-Candoni et al. published in *Langmuir,* 1999, 15 (19), pp 6563-6574 reports the impact of surfactant solutions drop on a low-surface-energy solid substrate investigated using a high-speed photographic technique (one picture every 100 μs) which allows simultaneous top and side views. The influence of physicochemical properties is analyzed by varying the adsorption kinetics of the surfactants and the initial diameter and velocity of the drop before impact.

Article titled "Wettability of a Glass Surface in the Presence of Two Nonionic Surfactant Mixtures" by K Szymczyk et al. published in *Langmuir;* 2008; 24(15): pp 7755-60 reports measurements of the advancing contact angle (theta) were carried out for aqueous solution of p-(1,1,3,3-tetramethylbutyl)phenoxypoly(ethylene glycol), Triton X-100 (TX100), and Triton X-165 (TX165) mixtures on glass.

Article tided "Controlling liquid splash on superhydrophobic surfaces by a vesicle surfactant" by M Song et al. published in *Science Advances;* 2017; 3 e1602188 reports that surfactant sodium bis(2-ethylhexyl) sulfosuccinate (called AOT) forms a vesicle at the air water interface and reduces the water surface tension rapidly resulting in controlling the splashing and retraction of drops on superhydrophobic surfaces.

Article titled "Enhancing droplet deposition through in-situ precipitation" by M Damak et al. published in *Nature Communications;* 2016; 7 12560 reports that simultaneous spraying of oppositely charged polyelectrolyte solutions results in formation of precipitates on surfaces and can control drop retraction on superhydrophobic surfaces.

Therefore, it is always desirable that hydrophobic surfaces need to be stained using an aqueous dispersion. Accordingly, the present inventors provide a method that uses certain combinations of nonionic surfactants which completely prevent retraction of aqueous drops impinging on hydrophobic surfaces.

Medical devices such as catheters or stents often have hydrophobic polymer surfaces. This poses challenges in the insertion of these devices in the human body as a high force needs to be applied by the surgeon. Therefore, there is a need to create coatings on the medical device surface that will render the surface hydrophilic and decrease the force for insertion in the body.

There is a general problem of known medical devices with hydrophilic coatings that water retention in the coating is too low, especially after leaching, or that the coating has poor adherence to the substrate, and/or that the means used for prolonging the water retention time and the adherence of the coating is too costly and/or harmful to the environment. Further, the known methods and coatings are affected by some problems. Such as production processes, involving different manners of incorporating the osmolality-increasing compounds in the coatings and costly. Further, the properties of the resulting, wetted hydrophilic surface coating to be inserted into the patient are at least to a certain extent affected by parameters of the wetting process.

WO2000067816 discloses a medical device for insertion into the body wherein said device has at least one surface which periodically comes into contact with a second surface, the first surface comprising a lubricious hydrophilic coating disposed thereon, said hydrophilic coating further comprising at least one antiblock agent, wherein said hydrophilic coating comprises at least one polymeric material selected from the group consisting of polyalkylene glycols, alkoxy polyalkylene glycols, copolymers of methylvinyl ether and maleic acid, poly(vinylpyrrolidone), poly(N-alkylacrylamide), poly(acrylic acid), poly(vinyl alcohol), poly(ethyleneimine), methyl cellulose, carboxymethyl cellulose, polyvinyl sulfonic acid, heparin, dextran, modified dextran and chondroitin sulphate and said antiblock agent is selected from the group consisting of long chain alkyl derivatives of fatty esters, fatty amides, fatty acid amides, fatty acids, fatty amines, alcohols, fatty acid alcohols, polyalkylene waxes, oxidized polyalkylene waxes, silicone waxes, silicone oils, alphaolefin sulfonates, phosphate ester of fatty alcohols, and mixtures thereof.

WO2011071629 discloses a coated medical device such as a balloon or stent and methods of manufacturing the device, where the device has a working length disposed between a distal end and a proximal end thereof; and a coating applied to at least a length of the body. The coating includes a hydrophobic therapeutic agent having a water solubility less than about 15.0 μg/ml and an emulsifier that is a solid at ambient temperature, wherein the emulsifiers include Tween 60, Vitamin E, Pluronic F68, Pluronic F127, Poloxamer 407, glycerol monostearate, Ascorbyl palmitate lecithin, egg yolk, phospholipid, phosphatidylcholine, polyethylene glycol-phosphatidyl ethanolamine conjugate or a combination thereof.

WO2005039770 discloses hydrophilic surfactant compositions that include a surfactant component and a stabilizer component. The surfactant can be coated on a surface by depositing a surfactant solution on at least a portion of the surface, then drying the surfactant solution to form the dry coating.

US20030207987 discloses the composition for applying a coating comprises sulfonated polyester, water, and a surface active agent. Methods for coating a medical implement comprise providing an aqueous dispersion comprising sulfonated polyester and surface active agent, contacting the medical implement with the aqueous dispersion, and drying the medical implement.

EP2241341A2 discloses a medical device coated with a composition comprising a therapeutic agent and a water soluble additive, which additive is at least one selected from a surfactant and a chemical compound having one or more hydroxyl, amino, carbonyl, carboxyl, acid, amide or ester groups and Log P of the therapeutic agent is higher than Log P of the additive for accelerate releasing of the therapeutic agent from the medical device.

U.S. Pat. No. 7,015,262 discloses a method for forming a hydrophilic coating on a medical implement, comprising: (a) providing an aqueous dispersion comprising sulfonated polyester and surface active agent; (b) contacting said medical implement in said aqueous dispersion; and (c) drying said medical implement.

US20130197435 discloses a coated medical device for rapid delivery of a therapeutic agent to a tissue in seconds to minutes. The medical device has a layer overlying the exterior surface of the medical device. The layer contains a therapeutic agent, at least one of an oil, a fatty acid, and a lipid, and an additive.

U.S. Pat. No. 6,610,035 discloses a medical device for insertion into the body wherein the device has at least one surface which periodically comes into contact with a second surface. The first surface comprises an improved lubricious coating having a first hydrogel layer and a second hydrophobic top coating which prevents the hydrogel coating from prematurely absorbing too much moisture.

Current solutions to this problem are based on polymeric coatings, such as polyurethanes, polyvinylpyrrolidone, polyacrylates, hyaluronic acid, etc. These typically involve curing a polymer coating on the surface and therefore there is considerable wastage since the polymer can start curing in the coating solution itself. In the prior art, polymeric coating has to be cured using heating or UV irradiation. Further, these coatings are available as dispersions with relatively low stability due to the tendency to cure. Therefore, there is considerable scope for improvement in this.

Therefore, to avoid prior art drawbacks, there is need for an improved substrate having improved lubricity and a coating method for providing medical devices with a hydrophilic surface coating, which is cost effective and which ensures that the hydrophilic coating can be adequately adhered. Accordingly, the present invention provides a medical device coated with hydrophilic coating prepared by a cost effective process which eliminates the need for curing.

OBJECTIVE OF THE INVENTION

The main objective of the present invention is to provide a method for preventing retraction of aqueous drops by pinning them on a hydrophobic surface.

Another objective of the present invention is to provide a medical device coated with a hydrophilic coating.

Yet another objective of the present invention is to provide a method for producing a medical device having a hydrophilic coating.

SUMMARY OF THE INVENTION

In an embodiment, the present invention provides a method for preventing retraction of an aqueous drop on a hydrophobic surface comprising the steps of:
  a) preparing a composition comprising a nonionic surfactant mixture having at least two surfactants dissolved in an aqueous media; and
  b) impinging said composition of step (a) on the hydrophobic surface;
wherein the ratio of water to surfactant in the surfactant mixture is in the range of 95:5 to 99.9:0.1 by weight and the aqueous drop retraction is less than 5%.

In an embodiment, the hydrophobic surface is selected from the group consisting of hydrophobic polymer, plant leaf, parafilm, surfaces covered with microcrystalline wax, hydrophobic biofilm, superhydrophobic surfaces that combine surface roughness with hydrophobic coating and surface functionalized using organosilane, organotitanate, and organozirconate.

In another embodiment, the hydrophobic polymeris selected from the group consisting of polyethylene, polypropylene, polystyrene, polycarbonate, aliphatic polyester and aromatic polyester, In one embodiment, the composition additionally comprises an active ingredient selected from the group consisting of molecular dyes such as pyrene, Nile Red, an antibiotic, a moisturizing compound and a particle dispersion such as colloids.

In another embodiment, the method helps in retaining the active ingredient on the hydrophobic surfaces after water washes.

In another embodiment, the surfactant mixture comprises at least two nonionic surfactants.

In yet another embodiment, the surfactant mixture comprises a first nonionic surfactant and a second nonionic surfactant.

In another embodiment, the weight of first nonionic surfactant in said surfactant mixture is in the range of 85 to 98%.

In still another embodiment, the weight of second nonionic surfactant in the surfactant mixture is in the range of 2 to 15%.

In another embodiment, the first nonionic surfactant is selected from the group consisting of a lipid, 37,11,15-tetramethyl-1,2,3 hexadecanetriol, phytanetriol, betaine, glycinate, amino propionate, and N-2-alkoxycarbonyl derivatives of N-methylglucamine or combinations thereof.

In another embodiment, the lipid is an unsaturated fatty acid monoglyceride selected from the group consisting of glycerol monooleate (HLB of 3.8), glycerol monostearate (HLB 3.4) and ethoxylated alcohol.

In another embodiment, the lipid is selected from the group consisting of a fatty acid, acyl glycerol, glycerolphospholipid, phosphatidic acid or salts thereof, phosphatidylethanolamine, phosphatidylcholine (lecithin), phosphatidylserine, phosphatidyllinositol, phosphatidylethanolamine, spingolipid (Ceramide), spingomyelin, cerebroside, glucocerebroside, ganglioside, steriod, cholesterol ester (stearate), sugar-based surfactant, glucolipid, and galactolipid, or combinations thereof.

In yet another embodiment, the second nonionic surfactant is a polymer selected from the group consisting of cellulose-derivative, hydrophobically-modified cellulose ester (e.g. emulsan), ethylene-oxide substituted chitin-derivative, starch-derivative, glycogen, glycoaminoglycan, keratin sulfate, dermatan sulfate, glycoprotein, lignan-based polymer, linear-substituted polymer, vinyl polymer, poly(acrylic acid), poly(acrylamide), polyamine, poly(ethylene imine), polyamide, polyisocyanate, polyester, poly(ethylene oxide), polyphosphonate, poly-siloxane, poly-carbonate, polyethoxylate, (PEO-PPO-PEO block copolymer), PEO-PPO diblock copolymer, PEO-PLA diblock copolymer, poloxamer, star polymer (dendrimer), poly-lysine, and lipoprotein or mixture thereof.

In another embodiment, the second nonionic surfactant is selected from the group consisting of Pluronic, Tween 20, Tween 40 and Tween 80.

In another embodiment, the present invention provides a medical device coated with a hydrophilic coating comprising a substrate and a coating composition of a nonionic surfactant mixture having at least two surfactants dissolved in an aqueous media.

In an embodiment, the medical device is selected from the group consisting of catheter, stent and medical gloves.

In another preferred embodiment, the coating composition enhances the lubricity of the substrate.

In one embodiment, the coating composition additionally contains an effective amount of a therapeutic agent.

In an embodiment, the coating composition comprises a surfactant mixture of at least two nonionic surfactants.

In another embodiment, the surfactant mixture comprises at least two nonionic surfactants.

In yet another embodiment, the surfactant mixture comprises a first nonionic surfactant and a second nonionic surfactant.

In another embodiment, the weight of first nonionic surfactant in the surfactant mixture is in the range of 85 to 98%.

In still another embodiment, the weight of second nonionic surfactant in the surfactant mixture is in the range of 2 to 15%.

In another embodiment, the first nonionic surfactant is selected from the group consisting of a lipid, 3,7,11,15-tetramethyl-1,2,3 hexadecanetriol, phytanetriol, betaine, glycinate, amino propionate, and N-2-alkoxycarbonyl derivatives of N-methylglucamine or combinations thereof.

In an embodiment, the lipid is an unsaturated fatty acid monoglyceride selected from the group consisting of glycerol monooleate (HLB of 3.8), glycerol monostearate (HLB 3.4) and ethoxylated alcohol.

In another embodiment, the lipid is selected from the group consisting of a fatty acid, acyl glycerol, glycerolphospholipid, phosphatidic acid or salts thereof, phosphatidylethanolamine phosphatidylcholine (lecithin), phosphatidylserine, phosphatidyllinositol, phosphatidylethanolamine, spingolipid (Ceramides), spingomyelin, cerebroside, glucocerebroside, ganglioside, steriod, cholesterol ester (stearates), sugar-based surfactant, glucolipid, and galactolipid, or combinations thereof.

In yet another embodiment, the second nonionic surfactant is a polymer selected from the group consisting of cellulose-derivative, hydrophobically-modified cellulose ester (e.g. emulsan), ethylene-oxide substituted chitin-derivative, starch-derivative, glycogen, glycoaminoglycan, keratin sulfate, dermatan sulfate, glycoprotein, lignan-based polymer, linear-substituted polymer, vinyl polymer, poly(acrylic acid), poly(acrylamide), polyamine, poly(ethylene imine), polyamide, polyisocyanate, polyester, poly(ethylene oxide), polyphosphonate, poly-siloxane, poly-carbonate, polyethoxylate, (PEO-PPO-PEO block copolymer), PEO-PPO diblock copolymer, PEO-PLA diblock copolymer, poloxamer, star polymer (dendrimer), poly-lysine, and lipoprotein or mixture thereof.

In an embodiment, said second nonionic surfactant is selected from the group consisting of Pluronic F127, Tween 20, Tween 40 and Tween 80.

In yet another embodiment, the present invention provides a method for producing a medical device coated with the hydrophilic coating comprising dipping a medical device into the coating composition of a surfactant mixture in an aqueous media followed by drying to afford the coated medical device.

In another embodiment, said process results in reduction of the contact angle of a water drop to less than about 20 degrees on the surface of medical device.

BRIEF DESCRIPTION OF ACCOMPANYING DRAWINGS

Figure 1D:
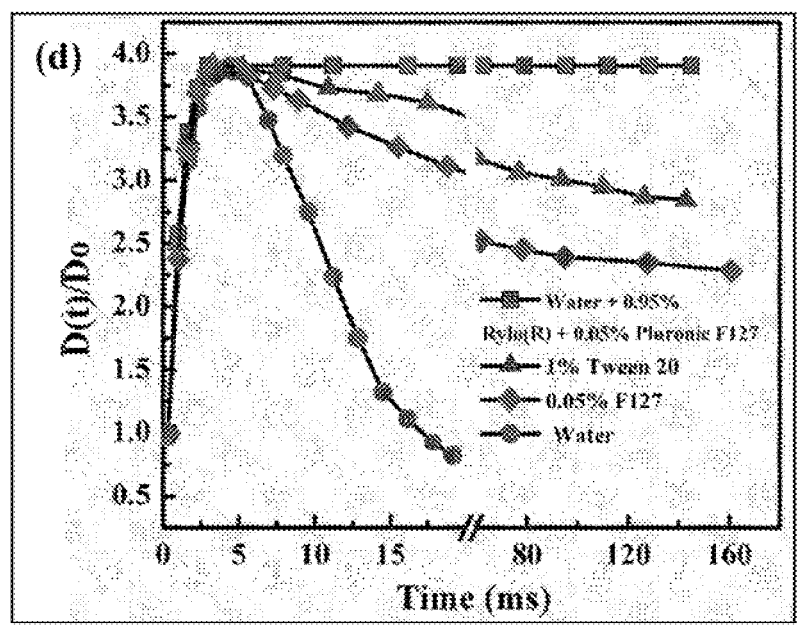

FIG. 1: Sequence of photographs shows the spreading of a drop of (a) water, (b) 1% Tween 20 and (c) 1% aqueous mixture of nonionic lipid, glycerol monooleate (GMO) and polymeric surfactant Pluronic F127 dispersion, on impacting ahydrophobizedglass surface. The photographs show the behaviour of the drop before impact (first panel) and at approximately 3, 20 and 120 ms after impact. The drop diameter before impact, $D_o \approx 2.25 \pm 0.1$ mm and the impact velocity, V=2.42 m/s in all experiments. (d) Time dependent drop size D(t), normalized by $D_o$, for drop impact experiments.

Figure 2:
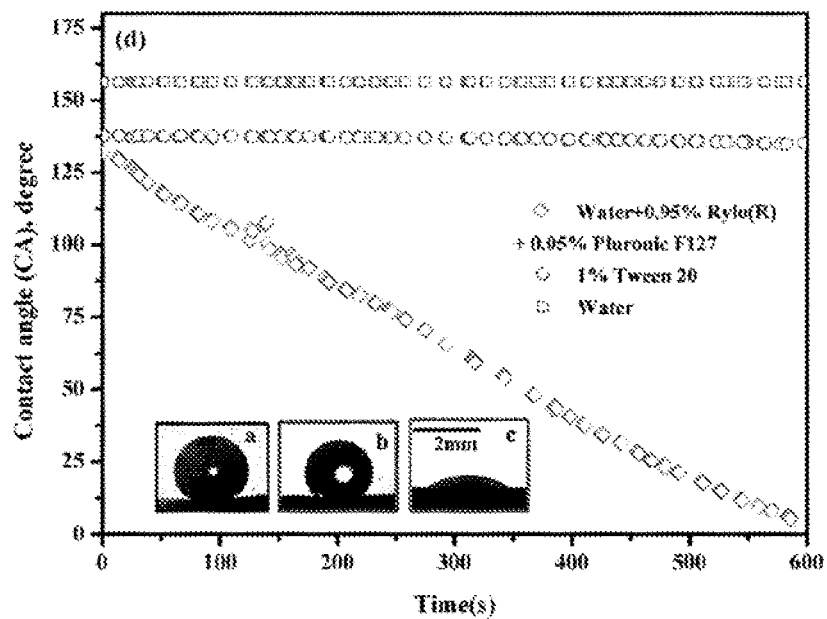

FIG. 2: Shape adopted on a horizontal lotus leaf of a 5 µl drop of (a) water (b) 1% Tween 20 and (c) aqueous mixture comprising 0.95% glycerol monooleate and 0.05% Pluronic F127. Images are taken 5 minutes after drop deposition on the leaf surface. (d) The contact angle for the water drop remains constant at =155 degrees over 10 minutes, while that for 1% aqueous mixture comprising 0.95% glycerol monooleate and 0.05% Pluronic F127 decreases continuously with time until the drop flattens on the lotus leaf surface.

Figure 3:
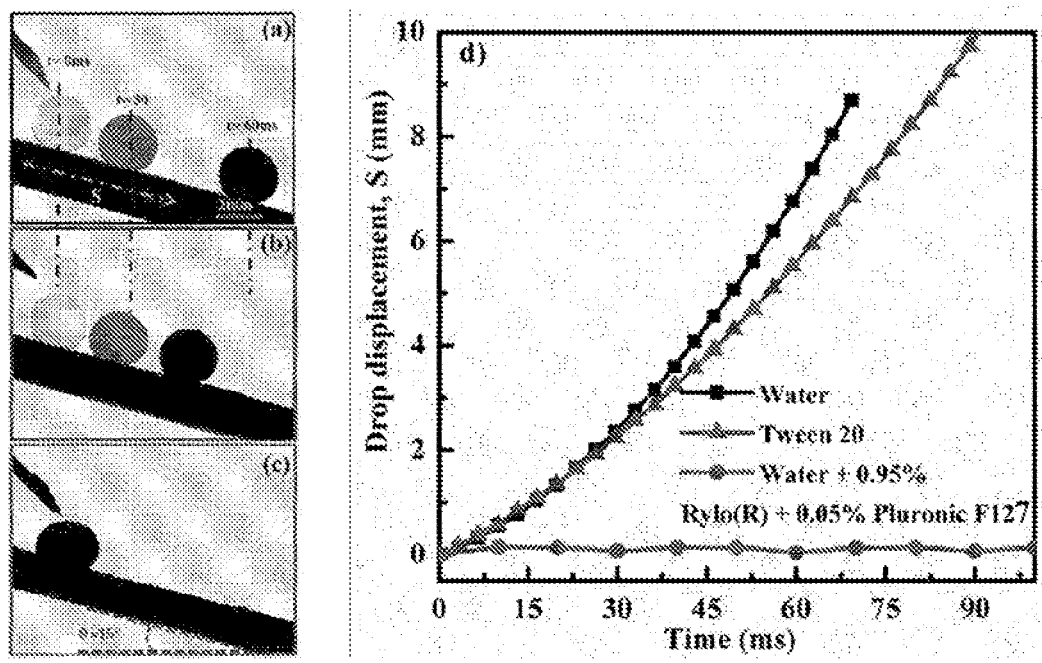

FIG. 3: Motion along an inclined lotus leaf (as described in the main text) of a drop of (a) water; (b) 1% aqueous Tween 20 and (c) 1% aqueous mixture comprising 0.95% glycerol monoleate and 0.05% Pluronic F127. The FIG. show the position of the drop as soon as it is placed on the leaf surface (t=0 ms), and after approximately 30 and 60 ms.(d) The displacement of the center of the drop along the inclined leaf surface is plotted for water, 1% Tween 20 and 1% aqueous mixture comprising 0.95% glycerol monooleate and 0.05% Pluronic F127 dispersion drops.

Figure 4:
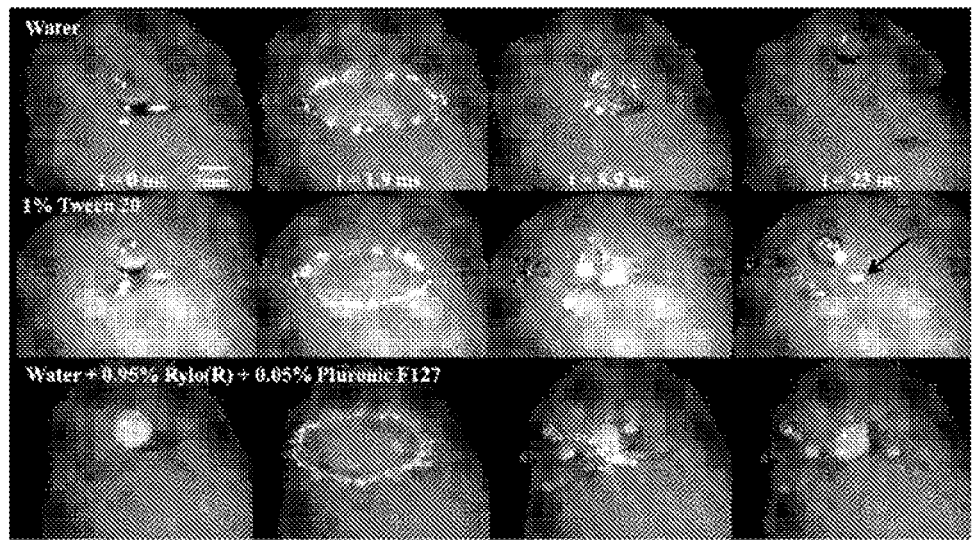

FIG. 4: Sequence of images shows the spreading of a drop of water (top layer), 1% Tween 20 (middle layer), and 1% aqueous mixture comprising 0.95% glycerol monooleate and 0.05% Pluronic F127 when impinged on a lotus leaf. The images show the behaviour of the drop before impact (first panel, t=0; $D_o$=2.20±0.02 mm) and at t=1.9, 8.9 and 23 ms (after impact). The arrow in the middle panel indicates a pinned droplet.

Figure 5:
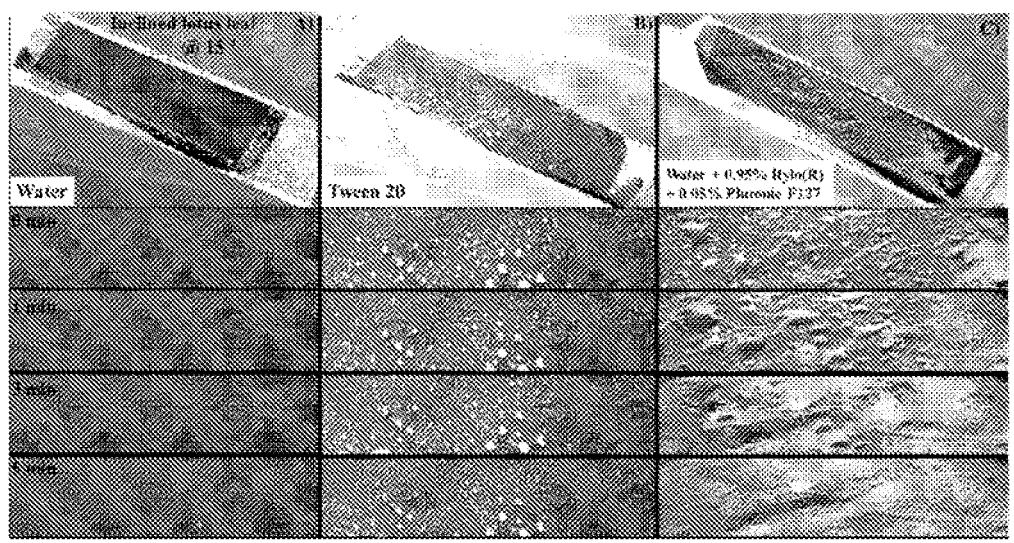

FIG. 5: Photographs showing the surface of an inclined lotus leaf that is sprayed with water (A): 1% aqueous Tween 20 (B) and 1% aqueous mixture comprising 0.95% glycerol monooleate and 0.05% Pluronic F127 dispersion (C). Data is presented as a function of time after spraying.

Figure 6A:
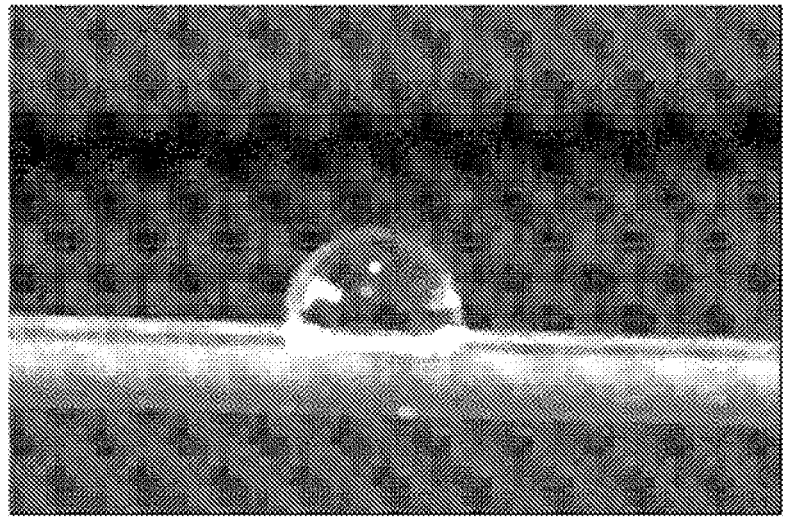
Figure 6B:
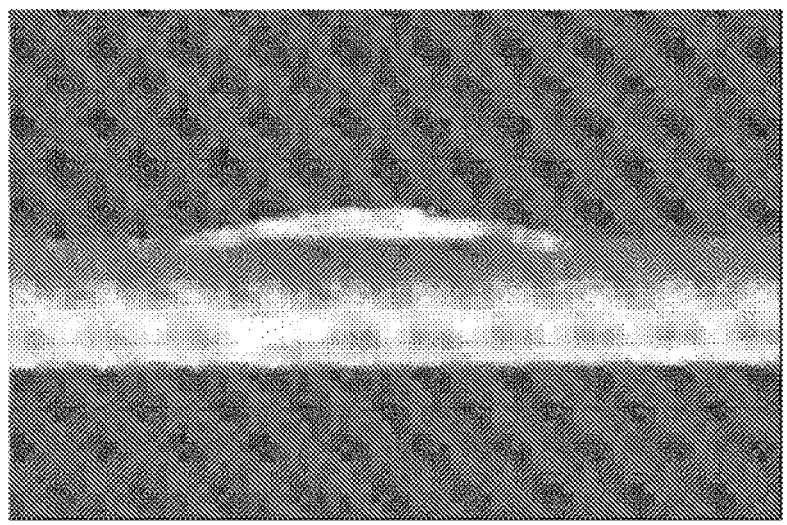

FIG. 6: Contact angle measurement experiment (A) Contact angle of water drop on unmodified polyethylene catheter. (Contact angle is near 100°). (B) Contact angle of water drop after surface modification of polyethylene catheter by surfactant mixture (Contact angle is near 15°).

Figure 7:
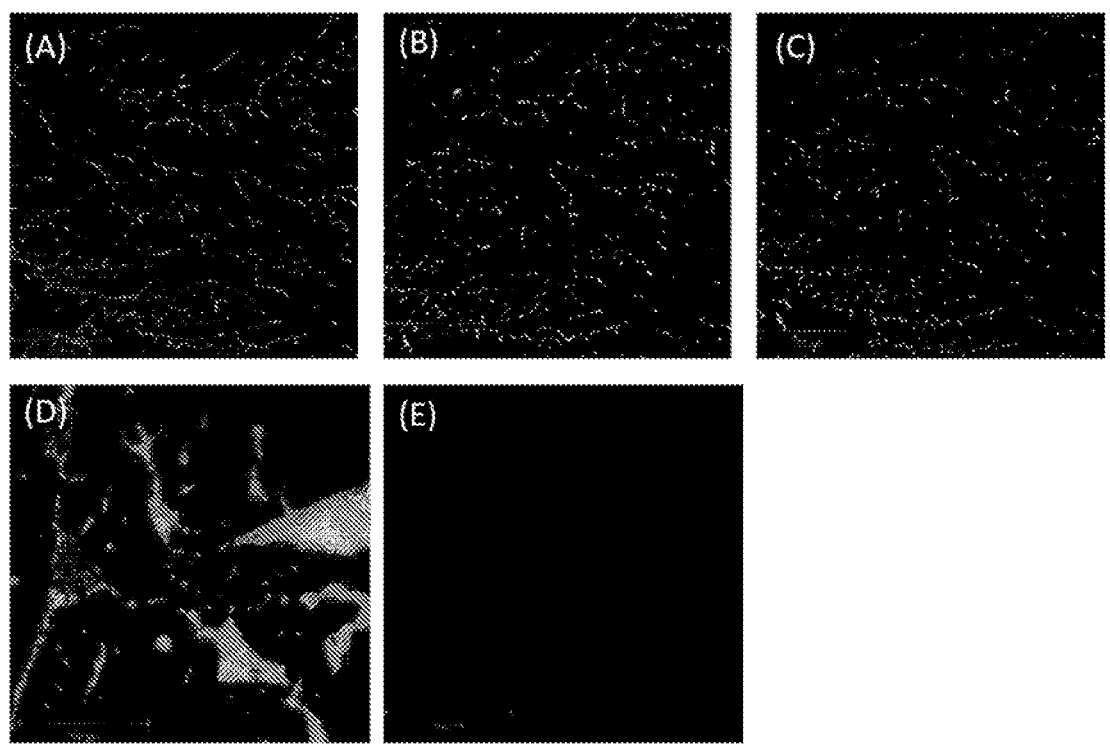

FIG. 7: An aqueous dispersion containing 0.95% (w/v) Rylo® and 0.05% (w/v) Pluronic F127 and 10 microliters of a 2.5% (w/v) dispersion of fluorescent 1 micron polystyrene latex particles (Fluo-Green from Microparticles GmbH, Germany) is taken and a drop is allowed to impinge and dry on a silane-hydrophobized glass slide. Fluorescent microscopy image are obtained (A) immediately after drying: (B) after 4 water washes and (C) after 7 water washes. In another experiment, an aqueous dispersion containing 10 microliters of a 2.5% (w/v) dispersion of fluorescent 1 micron polystyrene latex particles (Fluo-Green from Microparticles GmbH, Germany) is taken and a drop is allowed to impinge and dry on a silane-hydrophobized glass slide. Fluorescent microscopy image are obtained (D) immediately after drying and (B) after a single water wash.

DETAILED DESCRIPTION OF THE INVENTION

The invention will now be described in detail in connection with certain preferred and optional embodiments, so that various aspects thereof may be more fully understood and appreciated.

The present invention provides a method for preventing retraction of an aqueous drop impinged on a hydrophobic surface, wherein the aqueous drop retraction is less than 5%.

In an embodiment, the present invention provides a method for preventing retraction of an aqueous drop on a hydrophobic surface comprising the steps of:
  a) preparing a composition comprising a surfactant mixture dissolved in an aqueous media; and
  b) impinging said composition of step (a) on the hydrophobic surface;

wherein the ratio of water to surfactant in the surfactant mixture is in the range of 95:5 to 99.9:0.1 by weight and the aqueous drop retraction is less than 5%.

In preferred embodiment, the hydrophobic surface is selected from the group consisting of hydrophobic polymer, plant leaf, parafilm, surface covered with microcrystalline wax, hydrophobic biofilm, superhydrophobic surface that combine surface roughness with hydrophobic coating or surface functionalized using organosilane, organotitanate, or organozirconate.

In another preferred embodiment, the hydrophobic polymer is selected from the group consisting of polyethylene, polypropylene, polystyrene, polycarbonate, aliphatic polyester and aromatic polyester.

In one embodiment, the composition in step (a) additionally comprises an active ingredient selected from the group consisting of molecular dyes such as pyrene, Nile Red, an antibiotic, a moisturizing compound and particle dispersions such as colloids.

In another embodiment, said method helps in retaining the active ingredient on the hydrophobic surfaces after water washes.

In another embodiment, the surfactant mixture comprises at least two nonionic surfactants.

In yet another preferred embodiment, the surfactant mixture comprises a first nonionic surfactant and a second nonionic surfactant.

In another preferred embodiment, the weight of first nonionic surfactant in said surfactant mixture is in the range of 85 to 98%.

In still another preferred embodiment, the weight of second nonionic surfactant in said surfactant mixture is in the range of 2 to 15%.

In another embodiment, said first nonionic surfactant is selected from the group consisting of a lipid, 3,7,11,15-tetramethyl-1,2,3 hexadecanetriol, phytanetriol, betaine, glycinate, amino propionates, and N-2-alkoxycarbonyl derivatives of N-methylglucamine or combinations thereof.

In preferred embodiment, the lipid is an unsaturated fatty acid monoglyceride selected from the group consisting of glycerol monooleate (HLB of 3.8), glycerol monostearate (HLB 3.4) and ethoxylated alcohol.

In another preferred embodiment, the lipid is selected from the group consisting of fatty acid, acyl glycerol, glycerolphospholipid, phosphatidic acid or salts thereof, phosphatidylethanolamine, phosphatidylcholine (lecithin), phosphatidylserine, phosphatidyllinositol, phosphatidylethanolamine, spingolipid (Ceramides), spingomyelin, cerebroside, glucocerebroside, ganglioside, steriod, cholesterol ester (stearates), sugar-based surfactant, glucolipid, and galactolipid, or combinations thereof.

In yet another embodiment, the second nonionic surfactant is a polymer selected from the group consisting of cellulose-derivative, hydrophobically-modified cellulose ester (emulsan), ethylene-oxide substituted chitin-derivative, starch-derivative, glycogen, glycoaminoglycan, keratin sulfate, dermatan sulfate, glycoprotein, lignan-based polymer, linear-substituted polymer, vinyl polymer, poly(acrylic acid), poly(acrylamide), polyamine, poly(ethylene imine), polyamide, polyisocyanate, polyester, poly(ethylene oxide), polyphosphonate, poly-siloxane, poly-carbonate, polyethoxylate, (PEO-PPO-PEO block copolymer), PEO-PPO diblock copolymer, PEO-PLA diblock copolymer, poloxamer, star polymers (dendrimers), poly-lysine, and lipoprotein or mixture thereof.

In preferred embodiment, the second nonionic surfactant is selected from the group consisting of Pluronic, Tween 20, Tween 40 and Tween 80.

The impingement of a drop of 1% aqueous mixture comprising 0.95% glycerol monooleate and 0.05% Pluronic F127 on a hydrophobic surface is carried out and compared with the behavior of drops of water and of aqueous surfactant (1% Tween 20). High speed video imaging reveals that the spreading of 1% aqueous mixture comprising 0.95% glycerol monooleate and 0.05% Pluronic F127, Tween 20 surfactant and water drops after impact is similar—however, retraction of lipid nanoparticle dispersions is qualitatively different (FIG. 1). The spreading of drops of 1% Tween 20 and 1% aqueous mixture comprising 0.95% glycerol monooleate and 0.05% Pluronic F127 is similar to that of water (FIGS. 1 b,c). It is observed that the time dependent spreading diameter (normalized by the initial drop size), $D(t)/D_o$, is largely indistinguishable for all three systems in the first few ms after impact, when the drops spread on the surface (FIG. 1d), further the drop retracts continuously, with a velocity≈0.7 m/s, and after 20 ms forms a liquid column with diameter smaller than that of the initial drop (FIG. 1 a, d). In a comparative experiment, it is observed that drops containing F127 in solution (at a concentration of 0.05%) retract after spreading on hydrophobized glass. The retardation of drop retraction by 0.05% F127 is much less effective than even 1% Tween 20 (Figure id).

The velocity of the drop at the substrate, v, is measured using high speed photography (v=2.4 m/s) and matches the calculated value=$\sqrt{2gh}$, where g is the gravitational acceleration and h is the height from which the drop falls onto the substrate. The diameter of the drop, D, as it spreads on the surface is measured using high speed photography. The plot $D/D_o$ as a function of time as the drop impinges on the substrate shows $D/D_o$ increases and reaches a maximum. After it reaches the maximum, it stays constant and does not change with time. The extent of retraction as the decrease in D at 100 ms after drop impingement relative to the maximum value attained after spreading.

A plot of the diameter of the drop as it spreads on the hydrophobic surface, D(t), normalized by the initial spherical drop diameter, just before impinging on the substrate Do is potted (FIG. 1). Immediately after impingement, the drop spreads on the surface and D(t)/Do increases with time. The drop diameter is observed using a high speed camera. The increase in diameter with time is identical, within experimental precision, for water and aqueous dispersions of 1% Tween 20, 0.05% Platonic F127 and a 1% combination of glycerol monooleate (95 parts) and Pluronic F127 (5 parts). The maximum drop diameter is achieved after about 3 ms. Subsequently, D(t)/Do decreases for water, and for the aqueous solutions of Tween 20 and Pluronic. The decrease in D(t)/Do is very rapid for the water droplet and decreases to a value less than 1, indicating extreme retraction and bouncing of the drop off the surface. For the solutions of Tween and Pluronic, D(t)/Do retracts by approximately 25% and approximately 35% from the maximum size. In contrast for the 1% glycerol monooleate/Pluronic mixture, no retraction from the maximum D(t)Do is observed. For the 1% Rylo/Pluronic mixture, viz, the retraction in the diameter is about 0%.

The measure the contact angle of liquid drops (volume=5 µl) gently placed on a horizontal lotus leaf surface (FIG. 2) is measured. Water drops show a contact angle, CA≈1 SS on the lotus leaf and the CA value does not change with time. A drop of 1% Tween 20 drop shows an initial CA≈143°, lower than for the water drop, and this CA decreases to about 137° over 10 minutes. The behaviour of the lipid dispersion drop is very different when compared with water and 1% Tween 20. For the 1% aqueous mixture comprising 0.95% glycerol monooleate and 0.05% Pluronic F127, the CA decreases dramatically with time. The drop of lipid dispersion starts with a CA≈130° that decreases to near 0° within 10 minutes.

The behaviour of a drop of diameter=2.2 mm, placed gently on an inclined lotus leaf surface is measured; using a needle positioned about 2 mm above the leaf surface. The leaf is laid flat and adhered to a glass slide inclined at 15° from the horizontal. Each experiment is performed on a fresh lotus leaf and all experiments are repeated at least thrice. When a drop of water is placed on the inclined lotus leaf, it rapidly rolls off (FIG. 3). The drop appears approximately spherical as it rolls off the leaf, with advancing and receding contact angles (ACA and RCA) that are nearly identical at 146±3° and 144.3±3°, respectively (Table 1).

The table 1 shows the receding (RCA) and advancing contact angle (ACA) for the drops of water, 1% Tween 20, and 1% aqueous mixture comprising 0.95% glycerol monooleate and 0.05% Pluronic F127 on the lotus leaf inclined at angle 15° with the horizontal. The lotus leaf was supported with the help of a glass slide.

| Liquid drop, Volume = 10 µl | Receding contact angle (RCA), degrees | Advancing contact angle (ACA), degrees |
| --- | --- | --- |
| Water | 144.3° ± 3° | 146.3° ± 3° |
| Tween 20 | 130.6° ± 3° | 144.3° ± 3° |
| 1% aqueous mixture comprising 0.95% glycerol monooleate and 0.05% Pluronic F127 | 106.7° ± 3° | 133° ± 3° |

When the lotus leaf is sprayed with water (FIG. 5 a), the super hydrophobic leaf surface is not wetted by the spray. Water droplets bounce and roll off the surface leaving the leaf dry. In the case of 1% Tween 20, a majority of the droplets that issue from the spray nozzle bounce off the leaf surface (FIG. 5b). However, a few droplets splinter and stay on the surface and facilitate the retention of subsequent drops that impinge on them. These coalesce and form larger drops. However, most of the spray is lost as mist as the drops break up on impact and no liquid film forms. When 1% aqueous mixture comprising 0.95% glycerol monooleate and 0.05% Pluronic F127 is sprayed, the droplets are retained on the surface and rapidly coalesce on the leaf surface to form a continuous wetting film (FIG. 5 c).

The present invention also provides a method for use in many applications such as coating, staining and painting of hydrophobic substrates. Further, the method can also be used for deposition of colloidal particles on a hydrophobic substrate, such that the adhesion of the colloidal particles is resistant to washing with water.

In another embodiment, the present invention provides a medical device coated with a hydrophilic coating comprising a substrate and a coating composition and a method for producing the same.

In yet another embodiment, the present invention provides a medical device coated with a hydrophilic coating comprising a substrate and a coating composition of a surfactant mixture dissolved in an aqueous media.

In preferred embodiment, the medical device is selected from the group consisting of catheter, stent and medical gloves.

In another preferred embodiment, the coating composition enhances the lubricity of said substrate.

In yet another preferred embodiment, the surfactant mixture comprises at least two nonionic surfactants.

In still another preferred embodiment, the surfactant mixture comprises a first nonionic surfactant and a second nonionic surfactant.

In another preferred embodiment, the weight of first nonionic surfactant in said surfactant mixture is in the range of 85 to 98%.

In yet another preferred embodiment, the weight of second nonionic surfactant in said surfactant mixture is in the range of 2 to 15%.

In another embodiment, the first nonionic surfactant is selected from the group consisting of a lipid, 3,7,11,15-tetramethyl-1,2,3 hexadecanetriol, phytanetriol, betaine, glycinate, amino propionate, and N-2-alkoxycarbonyl derivatives of N-methylglucamine or combinations thereof.

In another preferred embodiment, said lipid is an unsaturated fatty acid monoglyceride selected from the group consisting of glycerol monooleate (HLB of 3.8), glycerol monostearate (HLB 3.4) and ethoxylated alcohol.

In another preferred embodiment, the lipid is selected from the group consisting of a fatty acid, acyl glycerol, glycerolphospholipid, phosphatidic acid or salts thereof, phosphatidylethanolamine, phosphatidylcholine (lecithin), phosphatidylserine, phosphatidyllinositol, phosphatidylethanolamine, spingolipid (Ceramide), spingomyelin, cerebroside, glucocerebroside, ganglioside, steriod, cholesterol ester (stearate), sugar-based surfactant, glucolipid, and galactolipid, or combinations thereof.

In yet another embodiment, the second nonionic surfactant is a polymer selected from the group consisting of cellulose-derivative, hydrophobically-modified cellulose ester (emulsan), ethylene-oxide substituted chitin-derivative, starch-derivative, glycogen, glycoaminoglycan, keratin sulfate, dermatan sulfate, glycoprotein, lignan-based polymer, linear-substituted polymer, vinyl polymer, poly(acrylic acid), poly(acrylamide), polyamine, poly(ethylene imine), polyamide, polyisocyanate, polyester, poly(ethylene oxide), polyphosphonate, poly-siloxane, poly-carbonate, poly-ethoxylate, (PEO-PPO-PEO block copolymer), PEO-PPO diblock copolymer, PEO-PLA diblock copolymer, poloxamer, star polymer (dendrimer), poly-lysine, and lipo-protein or mixture thereof.

In preferred embodiment, the second nonionic surfactant is selected from the group consisting of Pluronic, Tween 20, Tween 40 and Tween 80.

In one embodiment, the coating composition additionally contains an effective amount of a therapeutic agent.

Specific examples of such therapeutic agents include anti-thrombogenic agents or other agents for suppressing acute thrombosis, stenosis or late restenosis in arteries such as heparin, streptokinase, urokinase, tissue plasminogen activator, anti-thromboxane $B_2$ agents, anti-B-thromboglobulin, prostaglandin E, aspirin, dipyridimol, anti-thromboxane A, agents, murine monoclonal antibody 7E3, triazolopyrimidine, ciprostene, hirudin, ticlopidine, nicorandil, and the like. Antiplatelet derived growth factor may be used as a therapeutic agent to suppress subintimal fibromuscular hyperplasia at an arterial stenosis site, or any other inhibitor of cell growth at the stenosis site may be used.

The therapeutic agent may be an antibiotic which may be applied by this invention, optionally in conjunction with a controlled release carrier for persistence, to an infected stent or any other source of localized infection within the body. Similarly, the therapeutic agent may comprise steroids for the purpose of suppressing inflammation or for other reasons in a localized tissue site.

In another embodiment, the present invention provides a method for producing a medical device coated with hydrophilic coating comprises dipping a medical device into the coating composition of a surfactant mixture in an aqueous media followed by drying to afford the coated medical device.

In preferred embodiment, the medical device is selected from a catheter or a stent.

In another preferred embodiment, the process results in reduction of the contact angle of a water drop to less than about 20 degrees on the surface of the medical device.

In one embodiment, a plastic catheter is taken and dipped in an aqueous mixture containing 1% (weight/volume) of a 95:5 mixture of glycerol monooleate and Pluronic F127. After dipping for 5 minutes, the catheter is withdrawn and allowed to air dry. The contact angle of a drop of water is measured for the as received plastic catheter (FIG. 6 A). After dipping and air drying, the contact angle of a drop of water on the catheter is observed to be reduced to 15° (FIG. 6 B).

The contact angle is measured by using ImageJ software (FIG. 6). The drop is photographed and this photograph is analyzed to obtain the contact angle of the water drop on the catheter surface. On the uncoated catheter, it is observed that water contact angle exceeds 100 degrees, indicating that the surface is highly non-wetting to water. However, after coating the contact angle of water on the coated catheter surface is reduced to 15 degrees. This indicates that the water drop is able to spread on the surface and that the surface is wetted by water.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Impingement of a GMO/Pluronic Aqueous Mixture on a Parafilm Substrate The GMO/F127 blend was prepared by mixing GMO and Pluronic (F127) in 100:5 ratio. The blend was mixed by stirring and heating it at 80° C. for 30 minutes. Finally the blend was added to water. For example, to prepare 10 g sample solution, 0.315 g of GMO/F127 blend (in 100:5 ratio) were mixed with 9.695 g of Di water. The GMO/F127/water blend was mixed using an Ultra Turrax T25 from IKA operated at 10000 rpm for 10-15 minutes to prepare a milky dispersion. This solution was then impinged on Parafilm®, viz, a hydrophobic substrate in the following manner. The solution was loaded into a syringe and a drop with approximate diameter, $D_o$=2 mm was issued from the needle at a height of 30 cm above the substrate. The velocity of the drop at the substrate, v, was measured using high speed photography (v=2.4 m/s) and matched the calculated value=√2 g h, where g is the gravitational acceleration and h is the height from which the drop falls onto the substrate. The diameter of the drop, D, as it spreads on the surface was measured using high speed photography. A plot of $D/D_o$ as a function of time as the drop impinges on the substrate was plotted. Initially, $D/D_o$ increases and reaches a maximum. After it reaches the maximum, it stays constant and does not change with time. The extent of retraction is defined as the decrease in D at 100 ms after drop impingement relative to the maximum value attained after spreading. In this experiment, the retraction was 0%.

Example 2: Impingement of a GMO/Pluronic Aqueous Mixture on a Parafilm Substrate To 10 ml of water was added, 90 mg of commercial material, Rylo®, comprising a mixture of glycerol monooleate (>95%) and 5% di and triglycerides and 10 mg of block copolymer. Pluronic® (F127, polyethylene oxide-block-polypropylene oxide-block polyethylene oxide tri-block copolymer). This was subjected to high shear mixing (at 20000 rpm in an IKA Ultra Turrax mixer). This solution was then impinged on Parafilm, viz, a hydrophobic substrate in the following manner. The solution was loaded into a syringe and a drop with approximate diameter. $D_o=2$ mm was issued from the needle at a height of 30 cm above the substrate. The velocity of the drop at the substrate, v, was measured using high speed photography (v=2.4 m/s) and matched the calculated value=$\sqrt{2}$ g h, where g is the gravitational acceleration and h is the height from which the drop falls onto the substrate. The diameter of the drop, D, as it spreads on the surface was measured using high speed photography. A plot of $D/D_o$ as a function of time as the drop impinges on the substrate was plotted. Initially. $D/D_o$ increases and reaches a maximum. After it reaches the maximum, it stays constant and does not change with time. The extent of retraction is defined as the decrease in D at 100 ms after drop impingement relative to the maximum value attained after spreading. In this experiment, the retraction was 0%.

Example 3: Preparation of Hydrophobic Surface

Firstly, the glass slides were cleaned using an acidic piranha etch. The etched slides were stored in water. Before hydrophobic modification, the etched glass slide were dried using inert $N_2$. Toluene was taken in a petri dish and the dry glass slide was dipped into it and placed on a magnetic/heating stirrer. Then, 10-15 d of octylsilane drops was added to the toluene while stirring. Silanization of the glass surface was carried out at 60° C. Finally the modified glass slide was rinsed with copious amounts of toluene to remove excess/unreacted octylsilane. Hydrophobization was confirmed by measuring the contact angle of water on the modified glass surface ($\theta=104\pm20$).

Example 4: Impingement of a Rylo/Tween-20 Aqueous Mixture on a Hydrophobically Modified Glass Slide To 10 ml of water was added, 95 mg of commercial material, Rylo®, comprising a mixture of glycerol monooleate (>95%) and 5% di and triglycerides and 5 mg of Tween 20 nonionic surfactant. This was subjected to high shear mixing (at 20000 rpm in an IKA Ultra Turrax mixer). This solution was then impinged on glass slide chemically modified with octadecyltriethoxysilane, viz, a hydrophobic substrate in the following manner. The solution was loaded into a syringe and a drop with approximate diameter, $D_o=2$ mm was issued from the needle at a height of 30 cm above the substrate. The velocity of the drop at the substrate, v, was measured using high speed photography (v=2.4 m/s) and matched the calculated value=$\sqrt{2}$ g h, where g is the gravitational acceleration and h is the height from which the drop falls onto the substrate. The diameter of the drop, D, as it spreads on the surface was measured using high speed photography. A plot $D/D_o$ as a function of time as the drop impinges on the substrate was plotted. Initially, $D/D_o$ increases and reaches a maximum. After it reaches the maximum, it stays constant and does not change with time. The extent of retraction is defined as the decrease in D at 100 ms after drop impingement relative to the maximum value attained after spreading. In this experiment, the retraction was 0%.

Example 5: Impingement of a Tween-20 Aqueous Mixture on a Hydrophobically Modified Glass Slide To 10 ml of water was added, 200 mg of Tween 20 nonionic surfactant. This was subjected to high shear mixing (at 20000 rpm in an IKA Ultra Turrax mixer). This solution was then impinged on a glass slide chemically modified with octadecyltriethoxysilane, viz, a hydrophobic substrate in the following manner. The solution was loaded into a syringe and a drop with approximate diameter, $D_o$, =2 mm was issued from the needle at a height of 30 cm above the substrate. The velocity of the drop at the substrate, v, was measured using high speed photography (v=24 m/s) and matched the calculated value $\sqrt{2}$ g h, where g is the gravitational acceleration and h is the height from which the drop falls onto the substrate. The diameter of the drop, D, as it spreads on the surface was measured using high speed photography. A plot of $D/D_o$ as a function of time as the drop impinges on the substrate was plotted. Initially, $D/D_o$ increases and reaches a maximum. After it reaches the maximum, it retracts with time. The extent of retraction is defined as the decrease in D at 100 ms after drop impingement relative to the maximum value attained after spreading. In this experiment, the retraction was 25%.

Example 6: Impingement of an SDS Aqueous Mixture on a Hydrophobically Modified Glass Slide To 10 ml of water was added, 200 my of SDS surfactant. This was subjected to high shear mixing (at 20000 rpm in an IKA Ultra Turrax mixer). This solution was then impinged on glass slide chemically modified with octadecyltriethoxysilane, viz, a hydrophobic substrate in the following manner. The solution was loaded into a syringe and a drop with approximate diameter, $D_o=2$ mm was issued from the needle at a height of 30 cm above the substrate. The velocity of the drop at the substrate, v, was measured using high speed photography (v=2.4 m/s) and matched the calculated value=42 g h, where g is the gravitational acceleration and h is the height from which the drop falls onto the substrate. The diameter of the drop. D, as it spreads on the surface was measured using high speed photography. A plot of $D/D_o$ as a function of time as the drop impinges on the substrate was plotted. Initially, $D/D_o$ increases and reaches a maximum. After it reaches the maximum, it retracts with time. The extent of retraction is defined as the decrease in D at 100 ms after drop impingement relative to the maximum value attained after spreading. In this experiment, the retraction was 25%.

Example 7: Impingement of an SDS/Tween-20 Aqueous Mixture on a Hydrophobically Modified Glass Slide To 10 ml of water was added, 95 mg of SDS surfactant and 5 mg of Tween 20 surfactant. This was subjected to high shear mixing (at 20000 rpm in an IKA Ultra Turrax mixer). This solution was then impinged on glass slide chemically modified with octadecyltriethoxysilane, viz, a hydrophobic substrate in the following manner. The solution was loaded into a syringe and a drop with approximate diameter, $D_o$=2 mm was issued from the needle at a height of 30 cm above the substrate. The velocity of the drop at the substrate, v, was measured using high speed photography (v=2.4 m/s) and matched the calculated value=√2 g h, where g is the gravitational acceleration and h is the height from which the drop falls onto the substrate. The diameter of the drop, D, as it spreads on the surface was measured using high speed photography. A plot of $D/D_o$ as a function of time as the drop impinges on the substrate was plotted. Initially, $D/D_o$ increases and reaches a maximum. After it reaches the maximum, it retracts with time. The extent of retraction is defined as the decrease in D at 100 ms after drop impingement relative to the maximum value attained after spreading. In this experiment, the retraction was 25%.

Example 8: Impingement of an SDS/Tween-20 Aqueous Mixture on a Hydrophobically Modified Glass Slide To 10 ml of water was added, 5 mg of SDS surfactant and 95 mg of Tween 20 surfactant. This was subjected to high shear mixing (at 20000 rpm in an IKA Ultra Turrax mixer). This solution was then impinged on glass slide chemically modified with octadecyltriethoxysilane, viz, a hydrophobic substrate in the following manner. The solution was loaded into a syringe and a drop with approximate diameter, $D_o$≈2 mm was issued from the needle at a height of 30 cm above the substrate. The velocity of the drop at the substrate, v, was measured using high speed photography (v=2.4 m/s) and matched the calculated value=√2 g h, where g is the gravitational acceleration and h is the height from which the drop falls onto the substrate. The diameter of the drop, D, as it spreads on the surface was measured using high speed photography. A plot of $D/D_o$ as a function of time as the drop impinges on the substrate was plotted. Initially, $D/D_o$ increases and reaches a maximum. After it reaches the maximum, it retracts with time. The extent of retraction is defined as the decrease in D at 100 ms after drop impingement relative to the maximum value attained after spreading. In this experiment, the retraction was 25%.

Example 9: Impingement of a Rylo/Pluronic/Nile Red Aqueous Mixture on a Hydrophobically Modified Glass Slide To 10 ml of water was added, 95 mg of commercial material, Rylo®, comprising a mixture of glycerol monooleate (>95%) and 5% di and triglycerides and 5 mg of block copolymer, Pluronic® (F127, polyethylene oxide-block-polypropylene oxide-block polyethylene oxide tri-block copolymer). To this was added 1 mg of Nile Red. This is subjected to high shear mixing (at 20000 rpm in an IKA Ultra Turrax mixer). The solution was loaded into a syringe and a drop with approximate diameter. $D_o$=2 mm was issued from the needle at a height of 10 cm above the substrate. The substrate was a hydrophobic glass slide (prepared by covalent modification of a glass surface with octadecyltriethoxysilane), and was placed at a tilt angle of 30° with respect to the ground (viz, at an angle of 600 relative to the direction of gravitational acceleration). The drop was impinged on the substrate. The drop did not roll off the substrate and dried at the spot where it impinged. Absorption measurements were used to estimate the dye concentration on the substrate after drop drying. The slide was rinsed repeatedly in water and the dye concentration was measured. It was observed that there was no measurable change in dye concentration on repeated (at least 5 times) washing of the substrate in water.

Example 10: Impingement of an Aqueous Drop Containing Rylo/Pluronic and Fluorescent Polystyrene Latex Particles on an Inclined Hydrophobic Glass Slide To 10 ml of water was added, 95 mg of commercial material, Rylo®, comprising a mixture of glycerol monooleate (>95%) and 5% di and triglycerides and 5 mg of block copolymer, Pluronic® (F127, polyethylene oxide-block-polypropylene oxide-block polyethylene oxide tri-block copolymer). To this was added 10 microliter of a 2.5% (w/v) dispersion of fluorescent 1 micron PS particles (obtained from Microparticles GmbH, Berlin, Germany). This was subjected to high shear mixing (at 20000 rpm in an IKA Ultra Turrax mixer). The solution was loaded into a syringe and a drop with approximate diameter, $D_o$=2 mm was issued from the needle at a height of 10 cm above the substrate. The substrate was a hydrophobic glass slide (prepared by covalent modification of a glass surface with octadecyltriethoxysilane), and was placed at a tilt angle of 30° with respect to the ground (viz, at an angle of 60° relative to the direction of gravitational acceleration). The drop was impinged on the substrate. The drop did not roll off the substrate and was pinned where it impinged, and subsequently dried at that spot. Fluorescence microscopy was used to estimate the number density of particles adsorbed on the substrate after drop drying. The slide was rinsed repeatedly in water and the particle number density was measured. It was observed that there was no measurable change in particle number density on repeated (at least 5 times) washing of the substrate in water.

Example 11: Impingement of an Aqueous Drop Containing Rylo/Pluronic and Polymer Microbead Particles on an Inclined Hydrophobic Glass Slide To 10 ml of water was added, 95 mg of commercial material, Rylo®, comprising a mixture of glycerol monooleate (>95%) and 5% di and triglycerides and 5 mg of block copolymer, Pluronic® (F127, polyethylene oxide-block-polypropylene oxide-block polyethylene oxide tri-block copolymer). To this was added 10 microliter of a 2.5% (w/v) dispersion of 40 micron polymer microbeads, typical of those used for controlled release applications. This was subjected to high shear mixing (at 20000 rpm in an IKA Ultra Turrax mixer). The solution was loaded into a syringe and a drop with approximate diameter. $D_o$=2 mm was issued from the needle at a height of 10 cm above the substrate. The substrate was a hydrophobic glass slide (prepared by covalent modification of a glass surface with octadecyltriethoxysilane), and was placed at a tilt angle of 30° with respect to the ground (viz, at an angle of 60° relative to the direction of gravitational acceleration). The drop was impinged on the substrate. The drop did not roll off the substrate and was pinned where it impinged, and subsequently dried at that spot. Optical microscopy was used to estimate the number density of particles adsorbed on the substrate after drop drying. The slide was rinsed repeatedly in water and the particle number density was measured. It was observed that there was no measurable change in particle number density on repeated (at least 5 times) washing of the substrate in water.

Example 12: Impingement of a Rylo/Pluronic Aqueous Mixture on a Bacterial Biofilm To 10 ml of water was added, 95 mg of commercial material, Rylo®, comprising a mixture of glycerol monooleate (>95%) and 5% di and triglycerides, 5 mg of block copolymer, Pluronic® (F127, polyethylene oxide-block-polypropylene oxide-block polyethylene oxide tri-block copolymer) and 5 mg of chlorhexidine. This was subjected to high shear mixing (at 20000 rpm in an IKA Ultra Turrax mixer). A bacterial biofilm of Bacillus subtilis colonies was prepared according to the method described in the following publication: Alexander K. Epstein, Boaz Pokroya, Agnese Seminara, and Joanna Aizenberg, Proceedings of the National Academy of Sciences (USA), 2011, 108 (3), 995-1000. In this publication, such biofilms have been characterized as being resistant to wetting by water as well as 80% ethanol and other organic solvents. The solution comprising Rylo, Pluronic and chlorhexidine was loaded into a syringe and a drop with approximate diameter, Do=2 mm was issued from the needle at a height of 3 cm above the biofilm substrate. The diameter of the drop, D, as it spread on the surface was measured using high speed photography. A plot of D/Do as a function of time as the drop impinges on the substrate was plotted. Initially, D/Do increases and reaches a maximum. The contact angle of the drop on the bacterial biofilm was measured and it was observed that the biofilm wetted, viz, the contact angle was less than 90°.

Example 13: Contact Angle (AOC) and Dynamic Surface Tension (ST) Measurements For contact angle measurements, "contact angle goniometer" system equipped with CCD camera was used. Image analysis was done using SCA20 software (both from Data physics Instruments, GmbH, Germany). Sessile drop method was used for these measurements where droplet of 5 μL of different liquids was gently placed on the hydrophobic glass surface and on the lotus leaf. Angle of contact was monitored 5 times in a second continually for 10 min time window. The measurement of dynamic surface tension was carried out with same setup of goniometer as contact angle measurement. Addition of precise liquid release system was made to create pendant drop of 10 μL in the setup. Measurements were done with rate of 10 times in a second for 10 min.

Example 14: Synthesis of Coated Catheter

To 10 ml of water was added, 95 mg of commercial material, Rylo®, comprising a mixture of glycerol monooleate (>95%) and 5% di and triglycerides and 5 mg of block copolymer, Pluronic® (F127, polyethylene oxide-block-polypropylene oxide-block polyethylene oxide tri-block copolymer). This was subjected to high shear mixing (at 20000 rpm in an IKA Ultra Turrax mixer). The plastic catheter was dipped into the coating solution for 5 minutes. Following this, the catheter was removed and allowed to air dry (27° C. 30 minutes).

Example 15: Measurement of Contact Angle

The catheter was taken and a 3 microliter drop of distilled deionized water was gently placed on it using a micropipette. The drop was photographed and this photograph was analyzed using ImageJ software to obtain the contact angle of the water drop on the catheter surface. On the uncoated catheter, it is observed that water contact angle exceeded 100 degrees, indicating that the surface was highly non-wetting to water. After coating, the contact angle of water on the coated catheter surface reduced to 15 degrees. This indicated that the water drop was able to spread on the surface and that the surface was wetted by water. (FIG. 6)

Example 16: Washing Off of Particles Deposited on Hydrophobic Glass Slide from Aqueous Dispersons To 10 ml of water was added 10 microliter of a 2.5% (w/v) dispersion of fluorescent 1 micron PS particles (obtained from Microparticles GmbH, Berlin, Germany). The dispersion was loaded into a syringe and a drop with approximate diameter, $D_o$=2 mm was issued from the needle at a height of 10 cm above the substrate. The substrate was a hydrophobic glass slide (prepared by covalent modification of a glass surface with octadecyltriethoxysilane) placed horizontally on the ground. The drop was impinged on the substrate, spread and subsequently dried. Fluorescence microscopy was used to estimate the number density of particles adsorbed on the substrate after drop drying. It was observed that drying resulted in a highly nonuniform distribution of particles on the substrate surface. The slide was then washed by dipping and vigorous shaking in a beaker of water. The slide was washed, dried and imaged. Particles deposited on the substrate surface were readily washed off and were not visible after a single water wash.

Example 17: Resistance to Washing Off of Particles Deposited on Hydrophobic Glass Slide from Aqueous Drops Containing Rylo/Pluronic To 10 ml of water was added, 95 mg of commercial material, Rylo®, comprising a mixture of glycerol monooleate (>95%) and 5% di and triglycerides and 5 mg of block copolymer, Pluronic® (F127, polyethylene oxide-block-polypropylene oxide-block polyethylene oxide tri-block copolymer). To this was added 10 microliter of a 2.5% (w/v) dispersion of fluorescent 1 micron PS particles (obtained from Microparticles GmbH, Berlin, Germany). This was subjected to high shear mixing (at 20000 rpm in an IKA Ultra Turrax mixer). The solution was loaded into a syringe and a drop with approximate diameter, $D_o$=2 mm was issued from the needle at a height of 10 cm above the substrate. The substrate was a hydrophobic glass slide (prepared by covalent modification of a glass surface with octadecyltriethoxysilane) placed horizontally on the ground. The drop was impinged on the substrate, spread and subsequently dried. Fluorescence microscopy was used to estimate the number density of particles adsorbed on the substrate after drop drying. It was observed that drying resulted in a uniform distribution of particles on the substrate surface. The slide was then washed by dipping and vigorous shaking in a beaker of water. The slide was washed several times, dried and imaged. There was no measurable change in the number density or distribution of drops after at least 4 to 7 washes.

Advantages of the Invention

1. Aqueous dispersions of nonionic surfactant combinations prevent retraction of drops after impinging on hydrophobic substrates 2. The method can be used in many applications such as coating, staining, painting of hydrophobic substrates.
3. This method can also be used for deposition of colloidal particles on a hydrophobic substrate, such that the adhesion of the colloidal particles is resistant to washing with water.
4. Enhancement of lubricity of the polymeric device
5. Enhancement of hydrophilicity
6. Coating does not require a curing step
7. Simplifies the coating process by eliminating the need for curing
8. Eliminates waste since the coating solution cannot self cure
9. The method of present invention also helps in retaining the active ingredient on a hydrophobic surfaces after water washes.

We claim:

1. A method for preventing retraction of an aqueous drop on a hydrophobic surface, the method consisting of the steps of:
   a) preparing a composition comprising a nonionic surfactant mixture having a first nonionic surfactant and a second nonionic surfactants dispersed in an aqueous media; and
   b) spraying said composition of step (a) on the hydrophobic surface; to deposit drops of said composition on the surface
   wherein the first nonionic surfactant is selected from the group consisting of 3,7,11,15-tetramethyl-1,2,3-hexadecanetriol, phytanetriol, and a lipid selected from glycerol monooleate (HLB of 3.8), and glycerol monostearate (HLB 3.4) and said second nonionic surfactant is selected from the group consisting of polysorbate 20, polysorbate 40, polysorbate 80 and a polymer selected from the group consisting of (PEO-PPO-PEO block copolymer), PEO-PPO diblock copolymer, poloxamers, or mixture thereof,
   wherein the first nonionic surfactant in said surfactant mixture has weight in the range of 85 to 98% by weight of the total surfactant mixture and the second nonionic surfactant in said surfactant mixture has weight in the range of 2 to 15% of total surfactant mixture;
   wherein the ratio of water to surfactant in the surfactant mixture is in the range of 95:5 to 99.9:0.1 by weight and the aqueous drop retraction is less than 5%; and
   wherein said hydrophobic surface is selected from the group consisting of plant leaf, surfaces covered with microcrystalline wax, hydrophobic biofilm, super hydrophobic surface that combine surface roughness with hydrophobic coating and surface functionalized using organosilane, organotitanate, or organozirconate.

2. The method as claimed in claim 1, wherein said composition in step (a) additionally comprises an active ingredient selected from the group consisting of pyrene, Nile Red, an antibiotic, a moisturizing compound and a particle dispersion.

3. The method as claimed in claim 2, wherein said method helps in retaining the active ingredient on the hydrophobic surfaces after water washes.

4. The method of claim 1 wherein said hydrophobic surface is a plant leaf.

* * * * *